United States Patent [19]

Friedman

[11] Patent Number: 5,849,266
[45] Date of Patent: *Dec. 15, 1998

[54] DENTAL COMPOSITION FOR HYPERSENSITIVE TEETH

[75] Inventor: Michael Friedman, Jerusalem, Israel

[73] Assignee: Perio Products Ltd., Jerusalem, Israel

[ * ] Notice: The term of this patent shall not extend beyond the expiration date of Pat. No. 5,403,577 and 5,139,768.

[21] Appl. No.: 416,378

[22] Filed: Apr. 4, 1995

Related U.S. Application Data

[63] Continuation of Ser. No. 898,096, Jun. 12, 1992, Pat. No. 5,403,577, which is a continuation of Ser. No. 662,985, Feb. 28, 1991, Pat. No. 5,139,768, which is a continuation of Ser. No. 532,328, Jun. 5, 1990, abandoned, which is a continuation-in-part of Ser. No. 304,091, Jan. 31, 1989, abandoned.

[51] Int. Cl.$^6$ .................................................. A61K 6/00
[52] U.S. Cl. .............................. 424/49; 424/52; 424/53; 424/54; 424/673; 424/679; 514/772.3; 514/781; 514/902; 514/782
[58] Field of Search .................... 424/45, 49, 53, 424/54, 52, 673, 679; 514/902, 781

[56] References Cited

U.S. PATENT DOCUMENTS

| | | | |
|---|---|---|---|
| 2,984,639 | 5/1961 | Stamberger et al. | 260/32.4 |
| 3,122,483 | 2/1964 | Rosenthal | 167/93 |
| 3,431,208 | 3/1969 | Bailey | 252/106 |
| 3,863,006 | 1/1975 | Hodosh | 424/49 |
| 3,956,480 | 5/1976 | Dichter | 424/54 |
| 3,988,434 | 10/1976 | Schole | 424/54 |
| 4,011,309 | 3/1977 | Lutz | 424/49 |
| 4,057,621 | 11/1977 | Pashley | 424/49 |
| 4,224,310 | 9/1980 | Shah | 424/54 |
| 4,315,779 | 2/1982 | Heyd | 106/35 |
| 4,339,430 | 7/1982 | Gaffer | 424/54 |
| 4,374,824 | 2/1983 | Wahmi | 424/58 |
| 4,415,549 | 11/1983 | Shah | 424/52 |
| 4,459,277 | 7/1984 | Kosti | 424/7.1 |
| 4,529,748 | 7/1985 | Wienecke | 523/120 |
| 4,568,535 | 2/1986 | Loesche | 424/19 |
| 4,631,185 | 12/1986 | Kim | 424/49 |
| 4,634,589 | 1/1987 | Scheller | 424/49 |
| 4,645,662 | 2/1987 | Nakashima et al. | 424/52 |
| 4,710,372 | 12/1987 | Scheller | 424/49 |
| 4,751,072 | 6/1988 | Kim | 424/49 |
| 4,772,470 | 9/1988 | Inoue | 424/435 |
| 4,775,525 | 10/1988 | Pera | 424/58 |
| 4,911,922 | 3/1990 | Masuhara et al. | 424/81 |
| 4,990,327 | 2/1991 | Neirinckx | 424/49 |
| 5,213,615 | 5/1993 | Michl | 106/35 |

FOREIGN PATENT DOCUMENTS

| | | |
|---|---|---|
| 0 128655 | 12/1984 | European Pat. Off. . |
| 0 223245 | 5/1987 | European Pat. Off. . |
| 0 241295 | 10/1987 | European Pat. Off. . |
| 0 264660 | 4/1988 | European Pat. Off. . |
| 990957 | 5/1965 | United Kingdom . |

OTHER PUBLICATIONS

"Duraphat Woelm," in: Rote Liste 1990 (Editio Cantor, ed. Bundesverband der Pharmazeutischen Industrie e. V.) entery 53001 (1990).

De Bruyn et al., "Floride varnishes," *J. Biol. Buccale* 15:71–82 (1987).

Fiedler H.P., "Kolophonium," in: Lexikon der Hilfsstoffe für Pharmazie, Kosmetik und angrenzende Gebiete: Der Pharmazeutische Betrieb, Band 9 (Editio Cantor) p. 527 (1981).

Friedman, M. et al., "Sustained Release Chlorhexidine Preparations for Topical Use," *IADR Prog, and Abstr.* 59:905, No. 72 (1980).

Friedman, M. et al., "Prevention of Plaque Accumulation by Local Application of Sustained Release Delivery System od Chlorhexidine," *J. Cont. Rel.* 1:157–160 (1984).

Friedman, M. e6t al., "Plaque Inhibition by Sustained Release of Chorhexidine from Removable Appliances," *J. Dent. Res.* 64:1319–1321 (1985).

Friedman, M. and Golomb, G., "New sustained release dosage form of chlorhexidine for dental use," *J. Periodont. Res.* 17:323–328 (1982).

Gurny et al., "Bioadhesive intraoral release system: design, testing and analysis," *Biomaterials* 5:336–40 (1984).

Kanig, J.L. and Goodman, H., "Evaluation Procedures for Film–Forming Materials Used in Pharmaceutical Applications," *J. Pharm. Sci.* 51:77–83 (1962).

"Natürliche Harze," in: Römpp's Chemie Lexikon (George Thieme Verlag, ed Prof. J. Falbe) pp. 2941–2942 (1989).

Soskolne, A. et al.,"New Sustained Release Dosage Form of Chlorhexidine for Dental Use," *J. Periodont. Res.* 18:330–336 (1983).

Vivadent Information, "Behandlungsmöglicheiten für sensible Zähne mit Vivadent Produkten," 1 page Oct. 1991.

Remington's Pharmaceutical Sciences, p. 1321, 1985–1990, Gennaro et al.

Primary Examiner—Thurman K. Page
Assistant Examiner—James M. Spear
Attorney, Agent, or Firm—Sterne Kessler Goldstein & Fox P.L.L.C.

[57] ABSTRACT

The invention relates to an oral composition for the treatment and prevention of dental hypersensitivity comprising an anti-hypersensitivity agent embedded in a sustained release carrier such as a cellulosic or hydrophobic polymer, and a method for the use of said composition in treating and preventing dental hypersensitivity. The invention also provides for the supplementation of said oral composition with an adhesive and a plasticizer to increase the effectiveness of the anti-hypersensitivity agent.

14 Claims, No Drawings

DENTAL COMPOSITION FOR HYPERSENSITIVE TEETH

CROSS-REFERENCE TO RELATED APPLICATIONS

This application is a continuation of Ser. No. 07/898,096, filed Jun. 12, 1992, now U.S. Pat. No. 5,403,577, which is a continuation of Ser. No. 07/662,985, filed Feb. 28, 1991, now U.S. Pat. No. 5,139,768, which is a continuation of Ser. No. 07/532,328, filed Jun. 5, 1990, abandoned, which is a continuation-in-part of Ser. No. 07/304,091, filed Jan. 31, 1989, abandoned.

FIELD OF THE INVENTION

The invention is directed to a dental composition for preventing hypersensitivity in teeth, and to a method for the use of such composition for the treatment of hypersensitive teeth.

BACKGROUND OF THE INVENTION

Dental hypersensitivity, especially that arising from dentin and cementum hypersensitivity, is a frequently encountered problem in dentistry and a very troublesome clinical complaint. Hypersensitivity may occur wherever the dentin or cementum of a tooth is exposed by attrition or abrasion, or when the tooth's fine root surface is exposed by periodontal disease. In about 12% of erupted teeth, there is a developmental lack of protective covering of cementum at the cementoenamel junction. As a result, when the exposed dentin is subjected to mechanical, thermal, chemical or osmotic stimuli, the sensory nerves of the teeth become excited and a very painful response results. For example, people with hypersensitive teeth find it very painful to orally ingest certain forms of nourishment, such as liquids or foods that are hot or cold, sweet, hypertonic or contain citric acid. Everyday stimuli such as brushing the teeth may also be painful.

Many attempts have been made to control hypersensitivity of the teeth. For example, U.S. Pat. No. 3,863,006 (Hodosh, M.) describes the use of potassium, lithium or sodium nitrate; U.S. Pat. No. 4,751,072 and U.S. Pat. No. 4,631,185 (both to Kim, S.) describe the use of potassium bicarbonate and potassium chloride; U.S. Pat. No. 4,710,372 and U.S. Pat. No. 4,634,589 (both to Scheller, H. U.) describe the use of hydroxyapatite or fluorapatite; U.S. Pat. No. 4,057,621 Pashley, D. H., et al.) describes the use of an alkali metal or ammonium oxalate; U.S. Pat. No. 4,415,549 (Shah, N. B.) describes the use of strontium EDTA, fluoride and ammonium glycyrrhizzinate; and, GB990957 (Rosenthal, M. W.) describes the use of strontium for the control of hypersensitivity. The use of strontium ions to treat hypersensitivity was also disclosed in U.S. Pat. Nos. 3,122, 483, 3,988,434 and 4,224,310.

However, although clinically the most effective for reducing tooth hypersensitivity, the use of strontium salts for the treatment of hypersensitivity is disliked by patients due to the tendency of strontium salts to leave an unacceptably salty taste or metallic taste in the mouth, even when used in a toothpaste form. Another major disadvantage of strontium dentifrice is the long period of time of application which is required to achieve the clinical effect.

A topical, sustained-release form of an agent capable of controlling dental hypersensitivity could help prevent undesirable taste side effects and still treat the hypersensitive condition. Such a dosage form would be able to release the agent controlling the hypersensitivity at a lower therapeutic level over a long period of time, for example, for weeks. Sustained localized release of the hypersensitivity agent, targeted directly to the hypersensitive site, would also solve the problem of the prolonged time and application currently required to obtain clinical effectiveness with strontium.

Sustained release of an agent to treat a dental disease, peridontal disease, has been reported to be achieved by embedding chlorhexidine in an ethyl cellulose polymer to form a varnish (Friedman, M., et al., *J. Perio. Res.* 17:323–328 (1982); Friedman, M., et al., *IADR Prog. and Abstr.* 59:No. 905 (1980); Soskolne, W. A., et al., *J. Perio. Res.* 18:330–336 (1983)). This dosage form was also used in the treatment of plaque prevention in patients wearing orthodontic appliances (Friedman, M., et al., *J. Dent. Res.* 64:1319–1321 (1985)). However, this treatment, termed a varnish because it is applied to the surface of the teeth or tissues, was not deemed useful for the long-term prevention of the dental condition. Thus a need exists for the identification of a varnish composition capable of supplying a dental agent in an efficacious sustained-release, long term dosage form.

Wahmi (U.S. Pat. No. 4,374,824) discloses dentifrices for cleaning and preserving teeth. Disclosed were compositions comprising ginger, magnesium silicate, sodium chloride, catechu, alum, seed and shell of sweet almond, pyrethrum, gum mastic, and tobacco. It was reported that gum mastic was added to the composition to assist in the prevention of tooth decay. The disclosed compositions were intended to be in the form of toothpaste or tooth powders. The Wahmi patent does not disclose the possible long-term anti-hypersensitivity effect of the compositions; further, application of the disclosed compositions two to three times per day is required for antiplaque activity.

Mastic has been used previously for other dental purposes. U.S. Pat. No. 4,668,188 (Wolfenson, G. B.) discloses the use of a curable mastic in the production of an oral impression tray for making impressions of teeth and jaw structures. Mastics have been used in the production of dental molds (U.S. Pat. No. 4,500,288, VonWeissenfluh, H.) and as an adhesive to secure dental articulators (U.S. Pat. Nos. 4,548,581 and 4,382,787, Hoffman, R. E.). U.S. Pat. Nos. 4,532,126 and 4,428,927 (Ebert, W. R., et al.) disclose chewable, filled, one-piece soft elastic gelatin capsules, made chewable by a masticatory substance, such as a synthetic mastic.

U.S. Pat. No. 4,459,277 (Kosti, C. M.) relates to novel plaque compositions for use in evaluating oral hygiene practices. In brief, the patent discloses a water-insoluble, water-immiscible dye emulsified in fine droplets or rupturable capsules. The patent discloses the use of mastic resin as well as alginates, and other gums as an insoluble media for dye dispersion. In particular, sodium carboxymethylcellulose is disclosed. Also disclosed is the possibility of incorporating antibacterial agents such as stannous fluoride into the compositions. Significantly, the Kosti patent is concerned with diagnostic rather than therapeutic applications. The patent fails to suggest compositions exhibiting long-term preventive activity for hypersensitive teeth.

The background art fails to identify any compositions of matter comprising an effective anti-hypersensitivity agent together with a long term sustained release carrier capable of providing efficacious levels of the anti-hypersensitivity agent, either alone or in combination with an adhesive polymer such as a mastic and a plasticizer such as polyethylene glycol, for use as a hypersensitivity preventative by humans and other animals, under conditions in which the anti-hypersensitivity agents have no undersirable side effects such as changes in taste sensations.

SUMMARY OF THE INVENTION

With this need in mind, the present inventor set out to find an anti-hypersensitivity composition capable of delivering efficacious levels of an agent effective against those dental conditions responsible for hypersensitivity, said composition being such that the active anti-hypersensitivity agent is released in a sustained, long-term fashion, without a salty or metallic taste, and such that the hypersensitivity composition has the property of long-term adhesion to the teeth, and such that the hypersensitivity composition remains plastic during the entire period of application. With this goal in mind, the inventor has discovered a hypersensitivity composition with these desirable characteristics using materials already approved by the F.D.A., the composition comprising a metal salt or other hypersensitivity agent embedded in a sustained release carrier composed of a cellulose or hydrophobic polymer, in a pharmaceutically acceptable vehicle, optionally containing a plasticizer such as polyethylene glycol and/or an adhesive polymer such as gum mastic.

The invention is further directed to a sustained-release dental hypersensitivity preventative varnish composition which comprises: (a) an agent capable of suppressing dental hypersensitivity, and (b) a sustained release ethyl cellulose or hydrophobic polymer, in a pharmaceutically acceptable vehicle, wherein such composition is capable of forming a film which adheres to a dental surface, and wherein such film which adheres to a dental surface is capable of providing efficacious levels of such agent for the treatment of such dental hypersensitivity for a suitable period of time.

DETAILED DESCRIPTION OF THE PREFERRED EMBODIMENTS

This invention relates to oral compositions that provide sustained, efficient, inexpensive, anti-hypersensitivity activity without deleterious or undesirable side effects, and methods for using such compositions.

By "sustained-release" is meant the continuous release of an active substance at efficacious levels for a suitable period of time, such as overnight. By a "suitable" period of time is meant a period of time sufficiently long to provide the desired treatment for hypersensitivity. The release of the active substance may be constant or pulsed, as long as efficacious levels of the active substance are provided to the surrounding milieu for the desired period of time.

By an "efficacious level" is meant a level or concentration of a drug or other active agent which is high enough to be effective in treating the condition the drug was designed to treat.

By "oral varnish" is meant a composition which is topically applied to a surface such as a tooth, and which dries as a film adhering to that surface, in a manner which resists removal under normal conditions, for example by saliva and unvoluntary mouth movements during sleep, and is mechanically removable, for example by brushing the teeth.

The compilation of the components of the aforementioned oral composition is based upon the specific properties of each of the individual components, wherein each component of the combination increases the antihypersensivity effectiveness of other members of the combination.

The oral composition of the invention assists in the prevention of dental hypersensitivity. A variety of anti-hypersensitivity agents are suitable for the present invention. Preferred is the use of strontium salts. Other anti-hypersensitivity agents useful in the composition of the invention include potassium, lithium or sodium nitrate, potassium bicarbonate, potassium chloride, hydroxyapatite, fluorapatite, ammonium oxalate, EDTA with fluoride, fluoride, and ammonium glycyrrhizzinate.

It is also a feature of this invention that the aforementioned anti-hypersensitivity agent is released to the hypersensitive site in a long-term sustained release manner so as to reduce the required frequency of use. This kind of release is accomplished by embedding the anti-hypersensitivity agent in a cellulosic or hydrophobic acrylic polymer to form a varnish for administration to the oral cavity. The use of these polymers has the additional advantage of minimizing side effects of the hypersensitivity agent. Preferred are the insoluble and inexpensive polymers: hydrophobic type (polyethylene, polymethacrylate, polyamide-nylon, poly (ethylene-vinyl acetate) cellulose nitrate, silicones and others). A preferred cellulosic polymer is ethyl cellulose.

Thus, in a preferred embodiment, an oral composition with the highly desirable characteristics mentioned above comprises an anti-hypersensitivity compound such as strontium, preferably strontium chloride, embedded in a sustained release cellulosic polymer such as ethyl cellulose, in a pharmaceutically effective vehicle. For example, strontium (1–5 parts) and ethyl cellulose (5–9 parts) may be dissolved in ethanol (80–120 parts) for the preparation of sustained release delivery systems. The efficacy of such preparations (see examples below) demonstrates that the anti-hypersensitivity agent is efficiently released from said varnish at efficacious levels for an overnight period. In another embodiment, combinations of strontium salts with another anti-hypersensitive agent are used.

For application to a dental surface, that is, a surface within the oral cavity such as the buccal and lingual surfaces of teeth, an ethanolic solution of the antisensitivity agent and cellulosic or hydrophobic polymer (containing up to 4% of the anti-hypersensitivity agent as used in the varnish) are applied with a soft brush or with a spray. The dry film is formed in situ, after application of the varnish to the tooth surface and evaporation of the solvent. Mouthwash forms are not suitable because of inefficient application of the composition to affected areas. Preferably, a film of 10–160 $\mu$m thick dries on the surface of the tooth.

Those skilled in the art of oral medicine will, without undue experimentation, be able to produce ranges of concentrations of other appropriate antisensitivity agents and sustained release polymers.

It is another feature of the invention that the oral compositions for hypersensitivity treatment and prevention also provide for additional desirable components. For example, the adhesiveness of the oral composition may be improved by the incorporation within said composition of gums such as gum mastic in a formulation providing from 1–20% by weight of the gum mastic. Other suitable mastics are disclosed in U.S. Pat. No. 4,315,779 to Heyd, D., et al., and U.S. Pat. No. 4,374,844 to Wahmi, H. V. R., et al.

In another formulation, other compositions may include demulcents/humectants (i.e., plasticizers) such as polyethylene glycol 400–4000, glycerol, sorbitol, or mineral oil in concentrations of about 1% by weight. Other humectants, detergents, or surface-active agents will be known to those skilled in the formulation of oral compositions.

Thus, in a preferred composition, the oral composition of the invention comprises strontium, ethyl cellulose polymer, an adhesive, a plasticizer, and solvent (i.e., aqueous ethanol). In a highly preferred formulation, gum mastic is also present. Water, flavorings, and coloring agents may also be present as required.

Having now generally described the invention, the same will become better understood by reference to certain specific examples which are included herein for purposes of illustration only and are not intended to be limiting unless otherwise specified.

EXAMPLE 1

Varnish Preparation

The following formulations (Table 1) were all prepared by the same general procedure as follows: ethyl cellulose and polyethylene glycol polymers were dissolved in the suitable solvent. After complete dissolution of the polymers, the additional components of the varnish were added.

Ethyl cellulose—EC
Polyethylene glycol—PEG
Strontium chloride—STR

TABLE 1

| MATERIAL/FORMULATION | | | | | | | | | |
|---|---|---|---|---|---|---|---|---|---|
| | I | II | III | IV | V | VI | VII | VIII | IX |
| STR (G) | 1.0 | 2.0 | 3.0 | 3.0 | 3.0 | 4.0 | 3.0 | 3.0 | 3.0 |
| EC-NF100 (G) | 8.5 | 7.0 | 6.0 | 6.0 | 6.0 | 5.0 | 6.0 | 6.0 | 6.0 |
| PEG 400 (G) | 0.5 | 1.0 | 1.0 | 1.0 | 1.0 | 1.0 | — | — | — |
| PEG 4000 (G) | — | — | — | — | — | — | 1.0 | — | — |
| GLYCEROL (G) | — | — | — | — | — | — | — | 1.0 | — |
| MINERAL OIL (G) | — | — | — | — | — | — | — | — | 1.0 |
| ETHANOL (C"C) | 100 | 100 | 100 | 80 | 120 | 100 | 100 | 100 | 100 |

The best formulation was No. IV. The concentration of strontium in No. IV is lower than that currently used in toothpaste and dental solutions which contain 10% strontium.

The Effect of Local Application of Sustained Release Varnish Containing Strontium on Hypersensitivity of Teeth The effects of local application of a sustained-release delivery system of strontium on hypersensitive teeth is shown in Table 2.

The study includes nine patients, among whom 55 teeth were treated. Patients applied to their teeth nightly the strontium varnish formulation No. IV from Table 1 and the teeth were tested again after 7 and 30 days. Sensitivity was rated on a scale of 0–5, with five being the highest sensitivity. None of the patients complained of a metallic or salty taste.

TABLE 2

The effect of local application of sustained-release varnish of strontium on hypersensitivity of teeth

| | Mechanical stimuli | | | Thermal stimuli | | |
|---|---|---|---|---|---|---|
| | day 0 | day 7 | day 30 | day 0 | day 7 | day 30 |
| Patient 1 | 4 | 2 | 2 | 5 | 4 | 3 |
| | 1 | 0 | 0 | 4 | 3 | 1 |
| | 3 | 3 | 2 | 3 | 1 | 0 |
| | 3 | 1 | 1 | 3 | 2 | 2 |
| | 2 | 1 | 0 | 3 | 1 | 0 |
| | 1 | 1 | 0 | 1 | 1 | 0 |
| | 4 | 3 | 2 | 4 | 4 | 1 |
| Patient 2 | 2 | 2 | 1 | 4 | 2 | 2 |
| | 4 | 3 | 4 | 5 | 5 | 4 |
| | 3 | 2 | 2 | 3 | 2 | 2 |
| Patient 3 | 5 | 4 | 3 | 5 | 4 | 4 |
| | 3 | 3 | 3 | 2 | 2 | 1 |
| | 3 | 3 | 2 | 2 | 2 | 1 |
| | 4 | 3 | 0 | 5 | 4 | 3 |
| | 1 | 1 | 0 | 2 | 2 | 1 |
| Patient 4 | 3 | 2 | 1 | 4 | 3 | 0 |
| | 1 | 1 | 0 | 3 | 3 | 2 |
| | 3 | 1 | 0 | 3 | 1 | 1 |
| Patient 5 | 5 | 4 | 3 | 5 | 3 | 3 |
| | 3 | 2 | 2 | 3 | 2 | 2 |
| | 3 | 2 | 2 | 4 | 4 | 3 |
| | 3 | 2 | 1 | 2 | 2 | 1 |
| | 3 | 3 | 1 | 3 | 3 | 1 |
| Patient 6 | 3 | 1 | 1 | 5 | 4 | 2 |

TABLE 2-continued

The effect of local application of sustained-release varnish of strontium on hypersensitivity of teeth

| | Mechanical stimuli | | | Thermal stimuli | | |
|---|---|---|---|---|---|---|
| | day 0 | day 7 | day 30 | day 0 | day 7 | day 30 |
| | 4 | 2 | 1 | 5 | 5 | 4 |
| | 4 | 3 | 1 | 5 | 5 | 5 |
| | 2 | 1 | 1 | 2 | 1 | 1 |
| | 4 | 2 | 1 | 4 | 2 | 1 |
| | 4 | 3 | 2 | 4 | 4 | 2 |
| | 2 | 2 | 0 | 1 | 0 | 1 |
| | 4 | 3 | 2 | 5 | 5 | 5 |
| | 2 | 1 | 0 | 3 | 3 | 3 |
| | 4 | 3 | 3 | 4 | 3 | 2 |
| | 3 | 2 | 3 | 4 | 4 | 3 |
| Patient 7 | 2 | 2 | 2 | 4 | 4 | 3 |
| | 1 | 1 | 1 | 4 | 3 | 3 |
| | 4 | 4 | 4 | 5 | 5 | 5 |
| | 5 | 5 | 4 | 5 | 4 | 4 |
| | 4 | 4 | 2 | 3 | 3 | 4 |
| Patient 8 | 4 | 3 | 1 | 5 | 4 | 2 |
| | 3 | 3 | 1 | 4 | 3 | 3 |
| | 3 | 3 | 0 | 5 | 3 | 3 |
| | 3 | 3 | 1 | 4 | 2 | 2 |
| | 3 | 3 | 1 | 5 | 5 | 2 |
| | 5 | 4 | 2 | 5 | 5 | 5 |
| | 3 | 2 | 1 | 4 | 2 | 1 |
| | 3 | 2 | 1 | 4 | 4 | 4 |
| Patient 9 | 2 | 0 | 0 | 3 | 2 | 1 |
| | 1 | 0 | 0 | 4 | 3 | 2 |
| | 3 | 1 | 0 | 5 | 4 | 3 |
| | 1 | 0 | 0 | 4 | 3 | 3 |
| | 2 | 1 | 1 | 4 | 3 | 2 |
| | 2 | 1 | 1 | 5 | 5 | 2 |
| | 2 | 2 | 1 | 3 | 3 | 3 |
| | 3 | 1 | 2 | 4 | 4 | 4 |
| Number: | 55 | 55 | 55 | 55 | 55 | 55 |
| Mean: | 2.94 | 2.13 | 1.33 | 3.80 | 3.09 | 2.33 |
| Median: | 3.00 | 2.00 | 1.00 | 4.00 | 3.00 | 2.00 |
| Standard Deviation: | 1.11 | 1.17 | 1.12 | 1.09 | 1.26 | 1.36 |

Statistical Evaluation

Mechanical Stimuli

Day 7—significantly different than day 0 ($PL10^{-6}$, pair t-test, two-tailed).

Day 30—significantly different than day 0 ($PL10^{-6}$, pair t-test, two-tailed).

Thermal Stimuli

Day 7—significantly different than day 0 (P<L10$^{-6}$, pair t-test, two-tailed).

Day 30—significantly different than day 0 (P<L10$^{-6}$, pair t-test, two-tailed).

The results in Table 2 show that most of the teeth varnished with a strontium-containing composition of the invention were no longer hypersensitive or showed significantly less hypersensitivity for as long as 30 days after beginning the application of the varnish on a daily basis.

Now having fully described the invention, it will be understood by those with skill in the art that the scope may be performed with a wide and equivalent range of conditions, parameters, and the like, without affecting the spirit or scope of the invention or any embodiment thereof.

What is claimed is:

1. A sustained-release dental hypersensitivity preventative varnish composition which comprises:

(a) an agent capable of suppressing dental hypersensitivity; and (b) a sustained-release ethyl cellulose or hydrophobic polymer completely dissolved in a pharmaceutically acceptable solvent, wherein said sustained-release hydrophobic polymer is selected from the group consisting of polyethylene, polyamide-nylon, poly(ethylene-vinyl acetate) cellulose nitrate and silicones, wherein said pharmaceutically acceptable solvent comprises a solvent selected from the group consisting of water, ethyl alcohol, and a mixture of ethyl alcohol and water; and wherein said composition forms a film which adheres to a dental surface upon removal of said solvent, and wherein said film which adheres to a dental surface is capable of providing efficacious levels of said agent for the treatment of said dental hypersensitivity for a suitable period of time.

2. The varnish composition of claim 1, wherein said agent capable of suppressing dental hypersensitivity is selected from the group consisting of a strontium salt, potassium, lithium or sodium nitrate, potassium bicarbonate, potassium chloride, hydroxyapatite, fluorapatite, ammonium oxalate, EDTA with fluoride, fluoride, and ammonium glycyrrhizzinate.

3. The varnish composition of claim 2, wherein said agent capable of suppressing dental hypersensitivity is a strontium salt.

4. A method of prevention of dental hypersensitivity comprising topical application of the varnish composition of claim 1 to the teeth or gingival tissues of an animal.

5. The varnish composition of claim 1, wherein said sustained release polymer is ethyl cellulose.

6. The method of claim 4, wherein said application is by brush.

7. The varnish composition of claim 1, which additionally contains an agent selected from the group consisting of a flavoring agent, surface active agent and coloring agent.

8. The varnish composition of claim 1, which additionally contains a plasticizer.

9. The varnish composition of claim 8, wherein said plasticizer is selected from the group consisting of polyethylene glycol, glycerol, sorbitol, and mineral oil.

10. The varnish composition of claim 1, which additionally contains an adhesive gum.

11. The varnish composition of claim 10, wherein said adhesive gum is gum mastic.

12. The method of claim 4, wherein said application is by spray.

13. The method of claim 4, wherein said animal is a human.

14. The method of claim 4, wherein said animal is a domesticated animal.

* * * * *

UNITED STATES PATENT AND TRADEMARK OFFICE
CERTIFICATE OF CORRECTION

PATENT NO. : 5,849,266

DATED : December 15, 1998

INVENTORS : Friedman, M.

It is certified that an error appears in the above-identified patent and that said Letters Patent is hereby corrected as shown below.

On the title page, item [73], Assignee:
Should read : Yissum Research Development Company of the Hebrew University of Jerusalem Signed and Sealed this Twenty-ninth Day of June, 1999

Attest:

Q. TODD DICKINSON

*Attesting Officer*

*Acting Commissioner of Patents and Trademarks*